(12) United States Patent
Kesavadas et al.

(10) Patent No.: US 9,601,025 B2
(45) Date of Patent: Mar. 21, 2017

(54) METHOD AND SYSTEM FOR AUTOMATIC TOOL POSITION DETERMINATION FOR MINIMALLY-INVASIVE SURGERY TRAINING

(75) Inventors: Thenkurussi Kesavadas, Clarence Center, NY (US); Khurshid Guru, East Amherst, NY (US)

(73) Assignees: Health Research, Inc., Buffalo, NY (US); The Research Foundation for The State University of New York, Amherst, NY (US)

( * ) Notice: Subject to any disclaimer, the term of this patent is extended or adjusted under 35 U.S.C. 154(b) by 626 days.

(21) Appl. No.: 13/806,889

(22) PCT Filed: May 26, 2011

(86) PCT No.: PCT/US2011/038206
§ 371 (c)(1),
(2), (4) Date: Jul. 17, 2013

(87) PCT Pub. No.: WO2011/150254
PCT Pub. Date: Dec. 1, 2011

(65) Prior Publication Data
US 2013/0288214 A1    Oct. 31, 2013

Related U.S. Application Data

(60) Provisional application No. 61/348,733, filed on May 26, 2010.

(51) Int. Cl.
*G09B 5/02* (2006.01)
*G09B 23/28* (2006.01)

(52) U.S. Cl.
CPC ............... *G09B 5/02* (2013.01); *G09B 23/28* (2013.01); *G09B 23/285* (2013.01)

(58) Field of Classification Search
CPC ...... G09B 23/285; G09B 19/24; G09B 23/28; G09B 5/02
See application file for complete search history.

(56) References Cited

PUBLICATIONS

Blum et al., Advanced Augmented Reality Feedback for Teaching 3D Tool Manipulation, http://citeseerx.ist.psu.edu/viewdoc/download;jessionid=C3403126B11D51CB124D922A39D99-AD7?doi=10.1.1.91.126&rep+rep1&type=pdf Jan. 1, 2007.
(Continued)

*Primary Examiner* — Timothy A Musselman
(74) *Attorney, Agent, or Firm* — Hodgson Russ LLP

(57) ABSTRACT

The present invention may be embodied as a method of minimally-invasive surgery ("MIS") training using a video of an MIS comprising the steps of providing a processor, a display, and a first input device. The method comprises the step of processing the video using the processor to determine a location of the first surgical tool in each of the frames, determining whether the configuration of the first input device substantially corresponds to the location of the first surgical tool in each frame of the video while the video is displayed. The present invention may be embodied as a system for MIS training. The system comprises a processor, a communication device, and a first input device in communication with the processor. The processor is programmed perform any or all of the described disclosed methods.

24 Claims, 10 Drawing Sheets

(56) References Cited

PUBLICATIONS

Regueras et al., Optimizacion de un metodo de deteccion y seguimiento de instrumental suirurgico en video laparoscopico, http://oa.upm.es/9279/1/INVE_MEM_2010_85829.pdf Jan. 1, 2010.

Cano et al., Laparoscopic Tool Tracking Method for Augmented Reality Surgical Applications, Biomedical Simulation, pp. 191-196. Jul. 7, 2008.

Rodriguez et al., Segmentacion y seguimiento de estructuras en imagenes laparoscopicas, Actas Del XXVI Congresso Anual de la Sociedad Espanola de Ingenieria Biomedica (CASEIB 2008). Jan. 1, 2008.

Rosen et al., Generalized Approach for Modeling Minimally Invasive Surgery as a Stochastic Process Using a Discrete Markov Model, IEEE Transactions on Biomedical Engineering, vol. 53, No. 3, pp. 399-413. Mar. 1, 2006.

Pezzementi et al., Articulated object tracking by rendering consistent appearance parts, 2009 IEEE International Conference on Robotics and Automation, ICRA, May 12-17, 2009. May 12, 2009.

Padoy, Workflow and Activity Modeling for Monitoring Surgical Procedures, www.theses.fr/2010NAN10025/document. Apr. 14, 2010.

Konrad et al., 3.10 Motion Detection and Estimation; 4.11 2D and 3D Motion Tracking in Digital Video, Handbook of Image and Video Processing (Second Edition), pp. 253-274, 491. Jan. 1, 2005.

Elhabia et al., Moving Object Detection in Spatial Domain using Background Removal Techniques—State-of-Art, Recent Patents on Computer Science, pp. 32-54. Jan. 1, 2008.

METHOD AND SYSTEM FOR AUTOMATIC TOOL POSITION DETERMINATION FOR MINIMALLY-INVASIVE SURGERY TRAINING

CROSS-REFERENCE TO RELATED APPLICATION

This application claims the benefit of priority to U.S. provisional patent application Ser. No. 61/348,733, filed May 26, 2010, now pending, the disclosure of which is incorporated herein by reference.

FIELD OF THE INVENTION

The invention relates to surgical training, and more particularly to training a person in performing minimally-invasive surgical procedures.

BACKGROUND OF THE INVENTION

Minimally invasive surgery ("MIS") has been accepted as a useful alternative to open surgery for many health conditions. While safer for the patient, MIS poses a number of unique challenges to the surgeon performing them. The challenges fall into two broad domains: (i) the cognitive domain, wherein the surgeon uses knowledge and prior experience to make decisions regarding the procedure; and (ii) the motor control domain, where the surgeon uses physical skills to carry out specific decisions made through their cognitive process. For example, in laparoscopic surgery, a type of MIS, the surgery is conducted through small incisions made in the thorax or the abdomen of the body. Since the surgery takes place inside the closed volume of the human body, a small flexible camera called an endoscope is inserted inside the body to provide visual feedback. This set up gives rise to a number of cognitive challenges that make this form of surgery especially challenging, including:

(1) lack of visual feedback—the visual feedback is provided by images captured through the endoscope and displayed on a screen, lacking depth information;

(2) poor image quality—since the procedure is carried out within closed body cavities, the images received from the endoscope is affected by a number of factors, including improper lighting, smoke from cauterization of tissue and lensing effects;

(3) landmarks—Unlike open surgery, anatomical landmarks are not readily discernible and it is difficult to get oriented and navigate correctly inside the body without making mistakes; and (4) patient differences—pathology and individual variations in physiology create visual differences in two bodies, this effect is amplified in MIS.

Some ramifications of the above described problems result in making the cognitive process of the surgeons exceedingly difficult. It is for the same reasons residents require extensive training with a number of procedures before they can graduate to performing surgery on their own.

Currently available simulators may train surgical residents for motor skill improvement. However, the current training methods do not adequately address the issue of improving the cognitive ability of the resident. Therefore, a resident typically gets acquainted with identifying anatomical landmarks by watching actual surgeries and training under a surgeon. This makes the learning curve slow, difficult, and expensive.

Previous disclosures show MIS training simulators which use the location of surgical tools within a video of an MIS surgery to provide guidance to a trainee. However, these previous training methods and systems generally require the surgical tool location to be manually determined by a technician/programmer before the video can be used. Such manual effort is time-consuming and expensive.

Accordingly, there is a need for a more cost-effective system and method for determining surgical tool position in a video. And a corresponding need for a training method and system that uses the cost-effective surgical tool tracking to better prepare a trainee by improving both the trainee's motor skills and cognitive skills.

BRIEF SUMMARY OF THE INVENTION

The present invention may be embodied as a method of minimally-invasive surgery ("MIS") training using a video of an MIS. The method comprises the step of providing a processor, a display in communication with the processor, and a first input device in communication with the processor. The method comprises the step of processing the video using the processor to determine a location of the first surgical tool in each of the frames. The method comprises determining whether the configuration of the first input device substantially corresponds to the location of the first surgical tool in each frame of the video while the video is displayed. The video may be paused if the configuration of the first input device does not substantially correspond to the location of the first surgical tool.

The method may further comprise providing a memory device and writing the location of the at least one surgical tool in each frame of the video to the memory device.

Processing the video to determine a location of the first surgical tool in each of the frames may comprise obtaining physical characteristic data of the at least one surgical tool. Processing the video may further comprise processing a first frame of the video to detect a plurality of features. At least one tool feature of the at least one surgical tool may be identified by using the physical characteristic data of the at least one surgical tool. A position of the at least one tool feature may be calculated in order to determine the location of the at least one surgical tool within the first frame. Processing the video may further comprise repeating each of the frame-specific steps for each frame of the video. Where the video is a stereoscopic video, algorithms related to stereo vision may be used to determine the three-dimensional location coordinates of the at least one surgical tool.

In another embodiment of the step of processing the video, at least two frames of the video may be processed to detect at least one object which changes location from a first frame of the at least two frames to a second frame of the at least two frames. Processing the video to detect at least one object which changes location, may comprise the step of calculating a velocity field of a plurality of sections of the at least two frames of the video. A predetermined threshold parameter may be used to identify and combine sections of the at least two frames having similar, non-zero velocity fields into at least one region of interest. A centroid of the at least one region of interest is determined as the location of the at least one object. The centroid may be determined in each frame of the video in order to determine the location of the at least one object in each frame.

The present invention may be embodied as a system for MIS training using a video of an MIS, the video having a plurality of frames, and a first surgical tool is visible in the video. The system comprises a processor having a memory.

The system further comprises a communication device in communication with the processor and capable of receiving a video such that the video may be processed by the processor. The system also comprises a first input device in communication with the processor. The processor is programmed perform any or all of the methods previously described.

The present invention may be embodied as a computer program for performing any of the methods described herein. The computer program may be embodied on a computer readable medium. The computer readable medium may be a computer network or a storage location (e.g., server, NAS, SAN, etc) attached to a computer network.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

Figure 3:
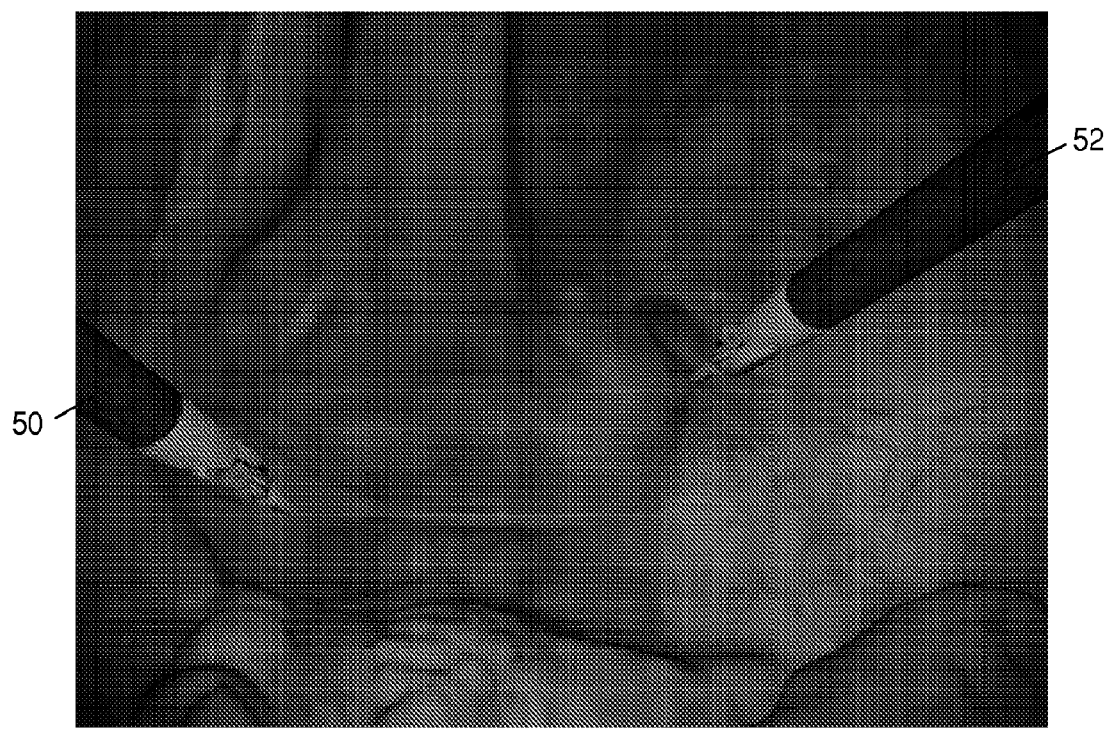
FIG. 3 is an image from a video of an MIS.

The present invention may be embodied as a method 100 of minimally-invasive surgery ("MIS") training using a video of an MIS. The video may be, for example, a video of a minimally-invasive surgery ("MIS") performed by a surgeon. In embodiments of the invention, the video itself, and capturing the video, are not a part of the method. Therefore, the video may be captured by a process outside of the present invention. The video may be pre-recorded on storage media (e.g., tape, disc, hard-drive, flash drive, etc.) as is known in the art, or the video may be a live video of a surgery being performed in real time. The video comprises a plurality of frames, where each frame is at least one image at a point in time. In an example, the video may show a prostatectomy using a da Vinci Surgical System® ("DVSS") where one of the robot's tools is visible. Such tools may include, but are not limited to, a scalpel, scissors, or bovie. An image of an exemplary video is shown in FIG. 3, wherein two surgical tools are visible. In another example, the video may show a conventional (non-robotic) laparoscopic procedure. Other videos of suitable MIS procedures will be apparent to those having skill in the art. In the video, at least one surgical tool is visible. The at least one surgical tool may be performing tasks such as, for example, grasping, suturing, cauterizing, etc.

The video may be a stereoscopic video, captured from two points-of-view in fixed relation to each other, in which case, each frame of the video may be considered to have two images. As such, the video is viewable as a "three-dimensional video." The three-dimensional representation is constructed from two two-dimensional images/videos. This type of three-dimensional construction is often referred to as 2.5-dimensional (two-and-a-half dimensional). The terms "three-dimensional" and "2.5-dimensional" may be used interchangeably in this disclosure.

The video may be pre-recorded by a surgeon and/or operating room staff during a surgical procedure. Alternatively, the video may be a video from a surgical procedure being performed at the same time as the MIS training according to the present invention—a "live feed." In another alternative, the video may be a video taken of a person using a surgical simulator to perform a surgery or other training tasks (e.g., a pick-and-place exercise). The method of capturing the video or the step of capturing the video does not make up a part of the present invention.

Figure 1A:
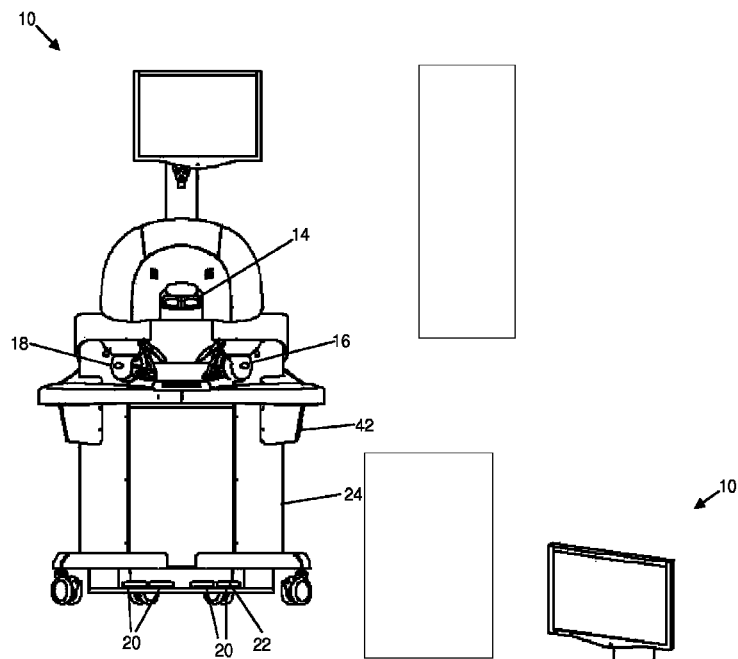
FIG. 1A is a front view of an MIS system according to an embodiment of the present invention.
Figure 1B:
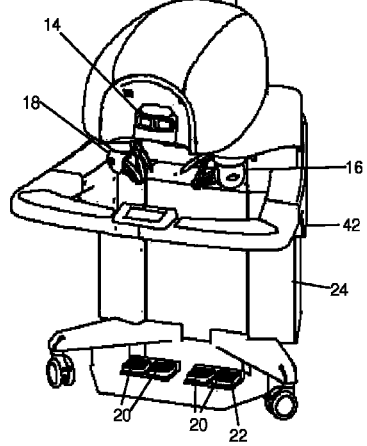
FIG. 1B is a perspective view of the MIS simulator of FIG. 1A.
Figure 2A:
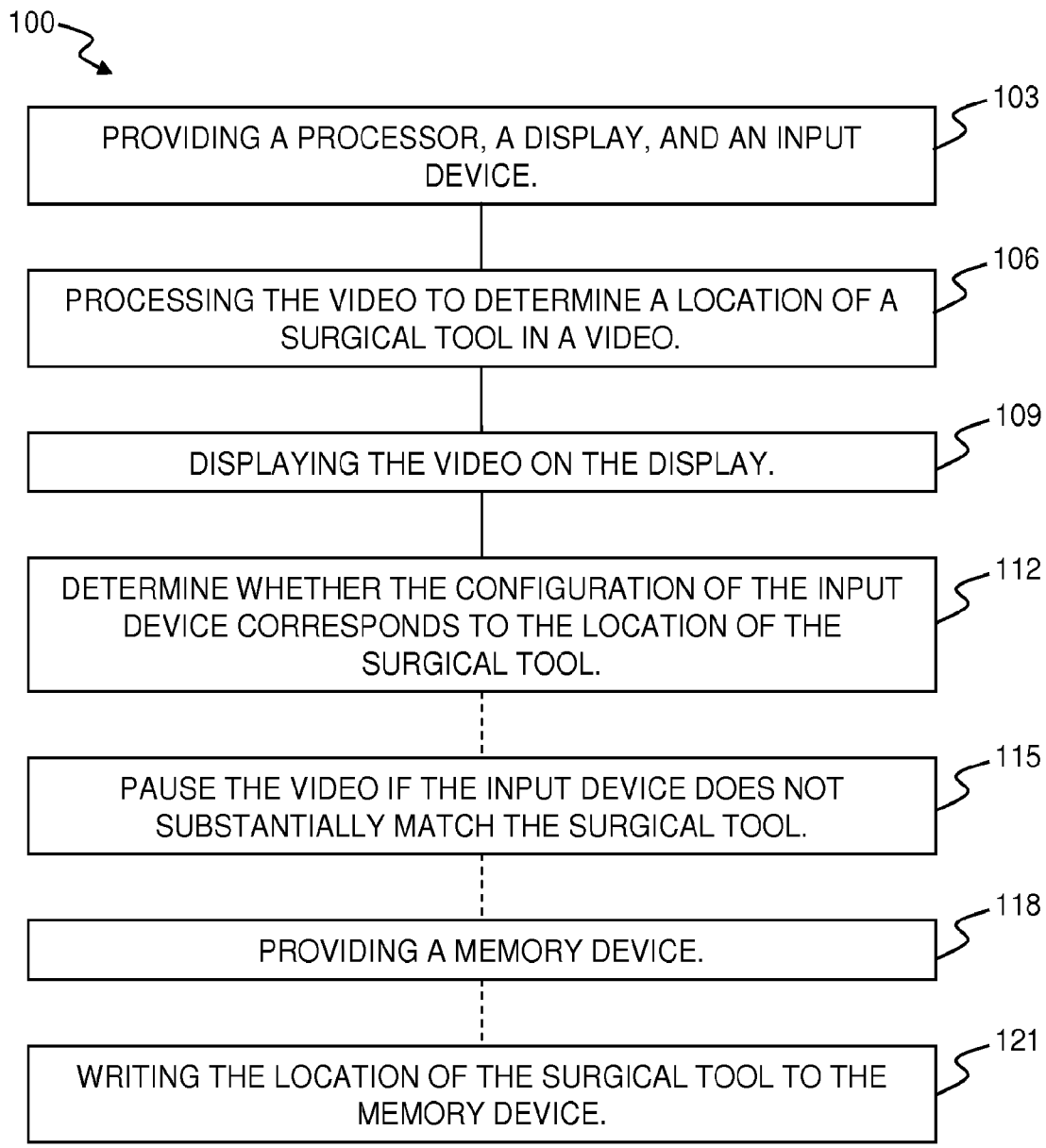
FIG. 2A is a flowchart of depicting a method according to another embodiment the present invention.
Figure 2B:
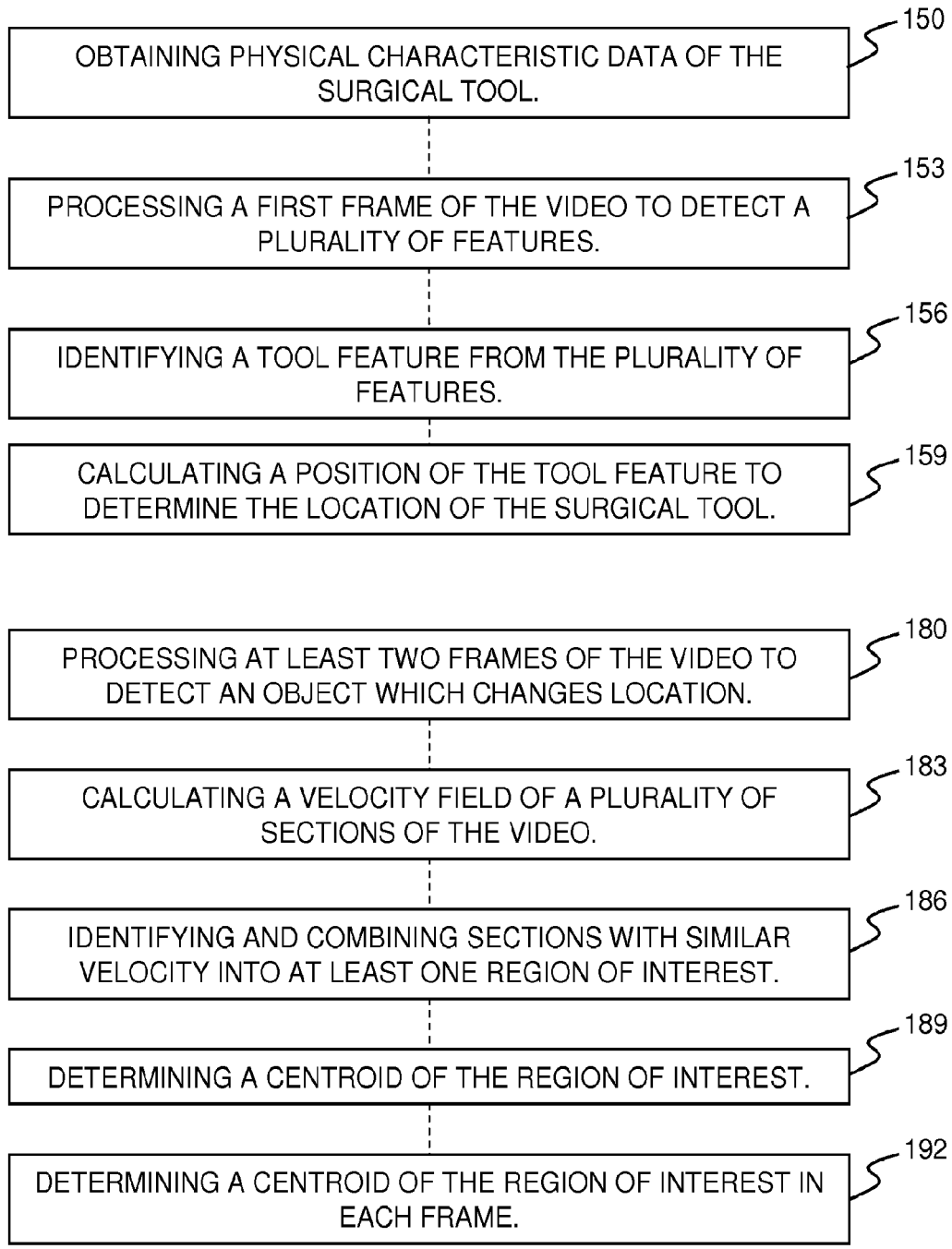
FIG. 2B is a flowchart of depicting other methods according to embodiments the present invention.

The method 100 comprises the step of providing 103 a processor, a display in communication with the processor, and a first input device in communication with the processor. An example system, a RoSS™ from Simulated Surgical Systems, LLC, is depicted in FIG. 1. Throughout this disclosure, reference will be made to this exemplary system, however, it should be understood that the RoSS simulator is one example and should not limit the present invention. In the system 10 of FIG. 1, the processor 24, the display 14, and the first input device 16 are shown. The display 14 may be a stereoscopic display as is known in the art (an example of which is depicted in FIG. 1). The first input device 16 may be selected to best recreate the motion of an actual surgical device. In a non-limiting example, a six degree-of-freedom device (such as, but not limited to, a PHANTOM® Omni®) may be selected as the first input device 16 to recreate the motion an input of a DVSS.

The method 100 comprises the step of processing 106 the video using the processor 24 to determine a location of the first surgical tool in each of the frames. Techniques for processing 106 the video are further described below. The method 100 comprises the step of displaying 109 the video on the display 14.

The method 100 comprises determining 112 whether the configuration of the first input device 16 substantially corresponds to the location of the first surgical tool in each frame of the video while the video is displayed. In use, a trainee watching the video play on the display 14 will manipulate the first input device 16 attempting to make motions which correspond to the motion of the first surgical tool on the screen and a determination made as to whether the motions (location at each point in time) substantially correspond. Additional training steps can be taken depending on whether the motions correspond or not. For example, the video may be paused 115 if the configuration of the first input device 16 does not substantially correspond to the location of the first surgical tool.

The method 100 may further comprise providing 118 a memory device and writing 121 the location of the at least one surgical tool in each frame of the video to the memory device.

Where a second surgical tool is visible in the video, a method of the present invention may (i) process the video using the computer to determine a location of each of the first and second surgical tools and (ii) additionally determine whether the configuration of a second input device substantially corresponds to the location of the second surgical tool in each frame of the video while the video is displayed.

Processing 106 the video to determine a location of the first surgical tool in each of the frames may comprise obtaining 150 physical characteristic data of the at least one surgical tool. The physical characteristic data may include information about the at least one surgical tool such as, but not limited to, color, length, width, diameter, shape, etc. The physical characteristic data may be in a machine-readable format, such as, for example, a delimited file. The physical data may be entered by a person using a data entry device.

Processing 106 the video may further comprise processing 153 a first frame of the video to detect a plurality of features. The features may be, for example but not limited to, edges, corners, points, regions of interest, or centroids of regions of interest. The features may be those portions of the video (or images of the video) which may be identified and/or tracked through image processing or video processing techniques (computer vision, etc.) Processing techniques are described further below and other processing techniques are known in the art.

At least one tool feature of the at least one surgical tool may be identified 156 by using the physical characteristic data of the at least one surgical tool. The detected plurality of features may be parsed to find the at least one tool feature. In a non-limiting example, with characteristic data of the length, width, and shape of the at least one surgical tool, a process embodying the present invention can identify a tool edge of appropriate length and spaced from, and roughly parallel to, another edge at an appropriate distance (corresponding to the width).

A position of the at least one tool feature may be calculated 159 in order to determine the location of the at least one surgical tool within the first frame. Processing 106 the video may further comprise repeating 162 each of the frame-specific steps 153, 156, 159 for each frame of the video. Therefore, a next frame will be processed 153 to identify features, at least one tool feature will be identified 156 using the physical characteristic data, and a position of the at least one tool feature is calculated 159 in order to determine the location of the at least one surgical tool within each frame. This tool position data in each frame of the video can further be used for analysis of trajectory and movements of the at least one surgical tool which is helpful for defining objective metrics during surgical training.

Where the video is a stereoscopic video, algorithms related to stereo vision may be used to determine 200 the three-dimensional location coordinates of the at least one surgical tool. For example, an algorithm such as, but not limited to, Kalman-Filter, may be used to determine three-dimensional coordinates.

In another embodiment of the step of processing 106 the video, at least two frames of the video may be processed 180 to detect at least one object which changes location from a first frame of the at least two frames to a second frame of the at least two frames. The object may be the at least one surgical tool. This process may be referred to as optical flow and an exemplary implementation is further described below ("Target Representation and Localization Example").

One embodiment of processing 180 the video to detect at least one object which changes location, comprises the step of calculating 183 a velocity field of a plurality of sections of the at least two frames of the video. A predetermined threshold parameter is used 186 to identify and combine sections of the at least two frames having similar, non-zero velocity fields into at least one region of interest. As such, sections of the at least two frames having similar (as defined by the predetermined threshold parameter), non-zero velocity fields are identified. The identified sections are combines. Each section may be an individual pixel or a group of pixels. A centroid of the at least one region of interest is determined 189 as the location of the at least one object. The centroid may be determined 192 in each frame of the video in order to determine the location of the at least one object in each frame. The at least one object may be the surgical tool.

Example Tracking Techniques

Two techniques for locating targets in video images are shown in detail as exemplary embodiments of the present invention. However, the present invention should not be limited by these examples.

"Target Representation and Localization" techniques may be viewed as bottom-up processes. These methods give a variety of tools for identifying the moving object. Locating and tracking the target object successfully is dependent on the algorithm. For example, using blob tracking is useful for identifying human movement because a person's profile changes dynamically. Typically the computational complexity for these algorithms is low.

"Filtering and Data Association" techniques are generally top-down processes, which involve incorporating prior information about the scene or object, addressing object dynamics, and evaluation of different hypotheses. These methods allow the tracking of complex objects along with more complex object interaction like tracking objects moving behind obstructions. The computational complexity for these algorithms is usually higher.

Filtering and Data Association Technique Example

The images (frames) which make up the video may be enhanced to cause the at least one surgical tool to better stand out from the background of the image. In some embodiments, the background of the image will be the surgical environment-tissues and other structures of the patient. Various image processing options are discussed below, including reference to a specific example (selection of image processing steps). The options and specific example are intended to be non-limiting. Other image processing techniques are known in the art and are within the scope of the present invention. In a method 100 of the present invention, one or more filters may be applied 115 to the frames of the video.

Reference is made to a specific example, where two needle tools are tracked. Each needle tool comprises a long shaft, having a base, and a wrist joint. The bases of the shafts are allowed to rotate freely. The video of this example is a stereoscopic video produced using two cameras slightly offset with respect to each other to produce set of images of the same scene from different angles. This stereoscopic video can be used to create a three-dimensional video of the MIS. The objective of this example was to track two surgical tools captured by two separate video cameras and find the locations of the tools. The following assumptions were made:

1. the tools may be described by features (e.g., color, number, length, etc.) which are known prior to analysis; and 2. the tools are the only objects which can be defined using straight lines.

Extract Images from Video Input

Videos are generally comprised of a plurality of still images taken over time. The video used by the present invention may first be parsed to extract the separate images (frames) from the video. In the present example, the openCV application programming interface ("API") was used to extract image frames from the video of tool motion captured by camera. Each of these images served as input for further image processing. In the present example, the video—and therefore each frame of the video—measured 720×486 pixels (a common, wide-screen format). FIG. 3 is a sample image showing two surgical tools 50, 52 and an internal portion of an abdomen of a patient. A method 100 of the present invention may comprise the step of extracting a frame from video, extracting each frame from the video successively, and/or extracting all frames from the video.

Retrieving Physical Characteristic Data

The properties (physical characteristics) of the tools were captured and retrieved for use during image processing (e.g., color (RGB format), length, width, etc.). The color information, if provided was used during thresholding (described below), while other properties were used during feature detection (described below). In the present example, the length of the tool shaft in a 720×486 resolution image is approximately 200 pixels.

Pre-Processing—Noise/Clutter

It may be beneficial to filter the image to reduce noise and clutter within the image. Noise can be defined as random errors in pixel brightness values, while clutter can be defined non-useful image components (patient tissue may involve a great deal of clutter). Both noise and clutter can be reduced by applying filters. For example, blurring (averaging) filters, Gaussian blur filters, and/or median filters may be applied to the image. Gaussian blur filters will remove high-frequencies from an image and may thus be considered to be low-pass filters. Median filters replace pixels with the median value of neighboring pixels according to rules which vary by filtering algorithm. Median filters reduce "impulse noise" considerably without excessive blurring of edges in the image. Both median and Gaussian filters are suited to noise/clutter reduction, however, median filters are better suited to preserving edges within an image. After considerable testing using different filters, the median filter technique was used for the present example.

Pre-Processing—Thresholding

In a method of the present invention, thresholding may be used to provide a binary image (or other quantized image). Thresholding is an image processing technique where pixels are assigned a new value based on its particular characteristic compared to a threshold value of that characteristic. For example, thresholding may assign a new value to a pixel based on the brightness of that pixel. In another examples, thresholding may assign a new value to a pixel based on its color (using an appropriate color space—e.g., red, green, blue ("RGB"), hue-saturation-luminosity ("HSL"), etc.). Thresholding is useful for producing binary images—images that have only two possible values for each pixel. In the present example, a binary image is well-suited for other steps, including edge detection.

Figure 4A:
FIG. 4A is the image of FIG. 3 after processing by gray level thresholding.
Figure 4B:
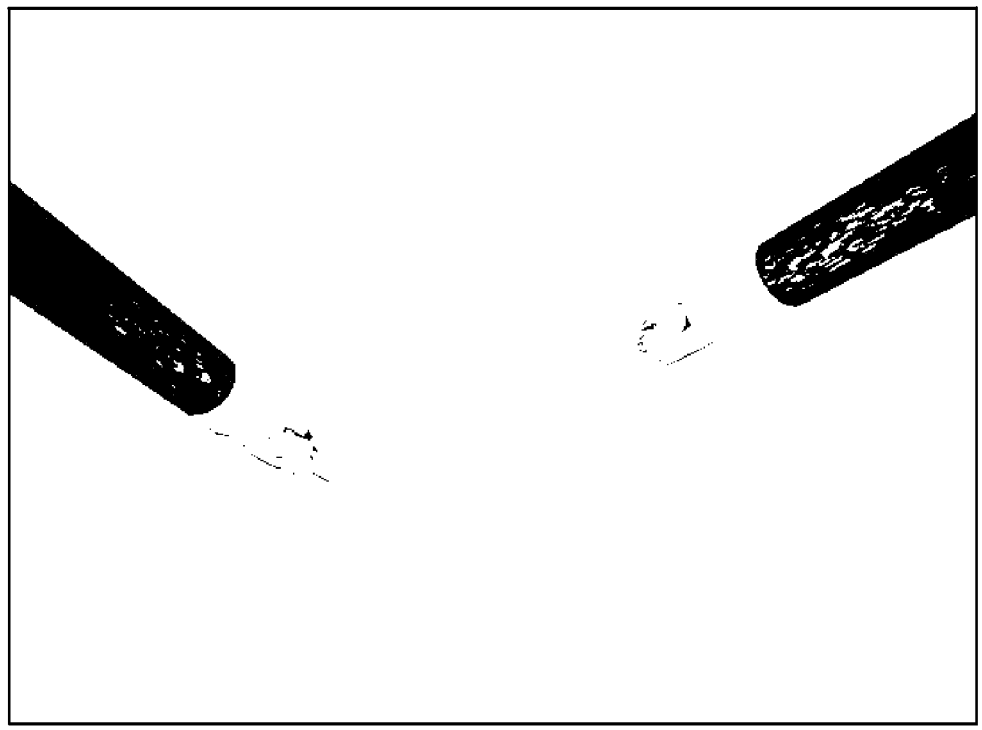
FIG. 4B is the image of FIG. 3 after processing by HSL thresholding.

In the present example, thresholding based on HSL value (FIG. 4B) proved to yield better results than brightness thresholding techniques (FIG. 4A). HSL thresholding is a useful method for achieving desirable results from color thresholding where an image was converted from another color space. A color space like HSL can result in a better-designed filter, as it allows the characteristics of color hue, saturation, and luminosity (brightness) to be addressed separately, i.e. allowing a more forgiving filter for luminosity if a large range of input brightness is anticipated. For certain data sets, HSL thresholding may render the noise/clutter reduction operation (described above) unnecessary. The output from thresholding based on HSL values provides a binary image with very few unwanted pixels.

Pre-Processing—Morphological Operations

A method of the present invention may use a morphological function to reduce the number of noise pixels and/or resolve discontinuities in the image. Erosion and dilation are methods of morphological operations which can be used independently or together to produce desired outputs. Erode will reduce the size of blobs of pixels in the image, and Dilate will increase the size of such blobs, either adding or subtracting pixels (their brightness value) from around the perimeter of the blob. For vision processing, these functions are useful because they can either accentuate or eliminate smaller blocks of pixels in the image. In addition, first applying Dilate and then Erode (called "Closing") can cause adjacent blobs of pixels to become connected, while application in the reverse order (called "Opening") can cause them to disconnect, without changing the general size of the blobs. Such morphological operations are suited to further reduce the number of noise pixels and/or reduce discontinuities in the image. For example, a few isolated pixels may be dilated to produce a uniform line. These operations operate best on binary images, although non-binary images may also be used. In morphological operations, a structural element (of a particular shape) is used to "probe" an image and reduce (erode) or expand (dilate) the shape of a structure in the image.

Erosion may be expressed as:

$$\text{Erosion}(A, B) = \bigcup_{b \in B} A_{-b} \qquad (1)$$

where A is the binary image and B is the structural element. When the structural element B has a center, the erosion of binary image A may be understood as the set of points reached by the center of B as B is moved within structures of the binary image A.

Dilation may be expressed as:

$$\text{Erosion}(A, B) = \bigcup_{b \in B} A_b. \qquad (2)$$

Where the structural element B has a center, the dilation of binary image A may be understood as the set of points reached by the periphery of B as the center of B is moved along structures of the binary image A.

Figure 5A:
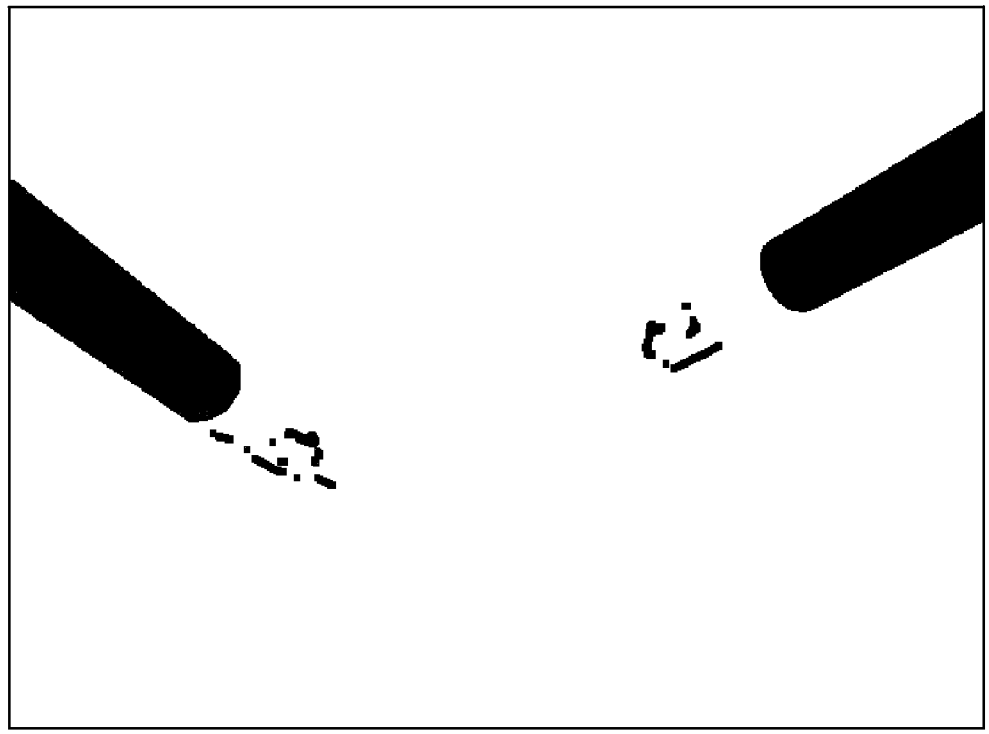
FIG. 5A is the image of FIG. 4B after processing by erosion.
Figure 5B:
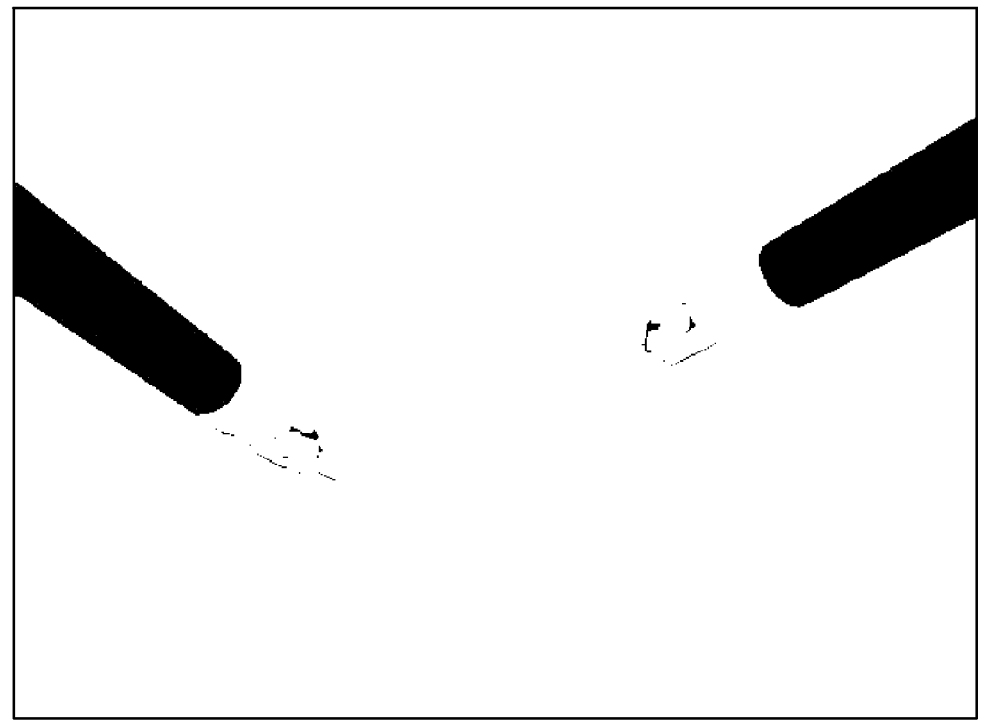
FIG. 5B is the image of FIG. 5A after processing by dilation.

In the present example, the image was first eroded and then dilated which connected disconnected pixels (see FIG. 5A (erosion) and FIG. 5B (dilation)).

Pre-Processing—Edge Detection

A method of the present invention may apply an edge detection function to the frames of the video. Edge detection involves scanning the image for places of sudden change (in color, brightness, or other appropriate characteristic), which usually denotes a division or an "edge." There are several methods that can be used, each performing better on different types of images. There are edge detection algorithms which use first derivative (usually search-based methods) and second order derivative (usually zero-crossing based methods) information. For example, algorithms using Sobel operators or Laplacian operators may be used to detect gradient variation, and thus edges.

Figure 6:
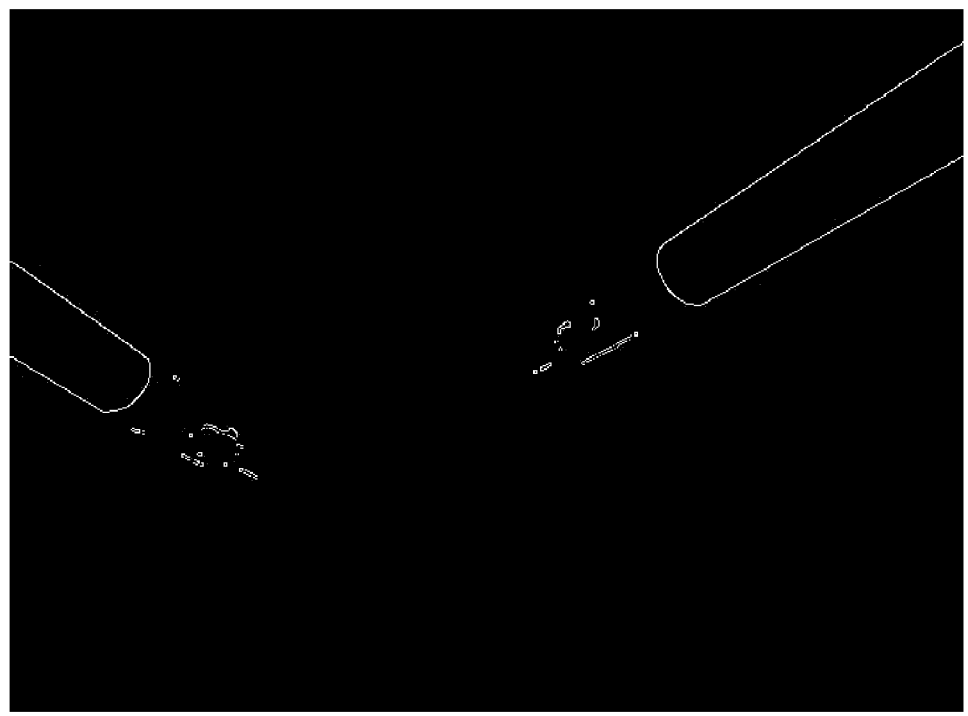
FIG. 6 is the image of FIG. 5B after processing by edge detection.

In the present example, the "Canny" edge detection algorithm was used. The Canny algorithm is a type of zero-crossing algorithm, meaning it checks the zero crossing of second order derivative. The Canny algorithm applies thresholding to the obtained output by applying a Sobel operator and creates a binary image comprising all possible edges in the image. Parameters may be selected in the function to refine the size of the edges. The sample image obtained from Canny Algorithm is shown in FIG. 6.

Pre-Processing—Hough Transform

A method of the present invention may use a Hough transform to determine a set of tool edge candidates from among a set of edges. A Hough transform is a technique for extracting features (in the present case, edges) from an image. Hough space is an image space that describes the probability that certain shapes exist at locations in an image. The OpenCV API contains two functions that make use of Hough transforms to identify instances of straight lines (cvHoughLines2) or circles (cvHoughCircles) within an image. Both functions require the input image to be grayscale/binary (single channel). The line function returns an array containing all possible lines, which is used for feature detection.

Figure 7:
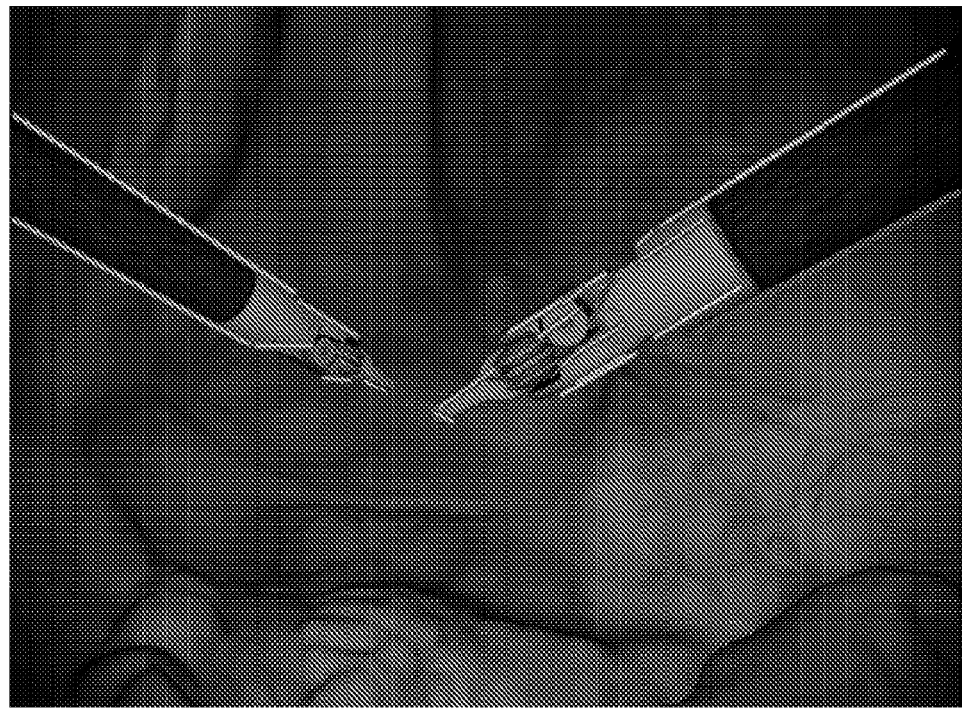
FIG. 7 is the image of FIG. 6 after further processing.

In the present example, cvHoughLines2 was used to determine the locations of lines existing in the image of FIG. 7. The resulting array may be considered a set of tool candidates. The set of tool candidates was used to recognize the tools based on the tool characteristics (physical characteristic data).

Feature Detection and Object Recognition

Figure 8:
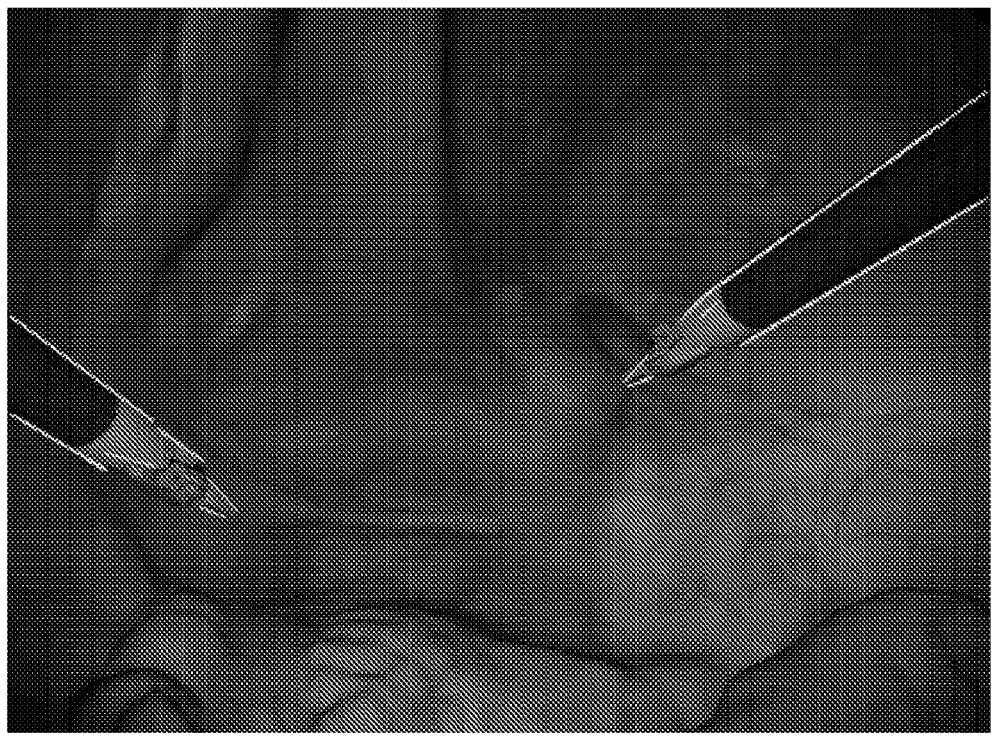
FIG. 8 is the image of FIG. 7 after using feature recognition techniques.

A method of the present invention may use the physical characteristic data to determine at least one tool edge from among the tool edge candidates. In the present example, after the set of tool candidates was determined from the image using the aforementioned techniques (or other appropriate techniques), the lines defining the surgical tools may be identified from among the set. The physical characteristic data was used. For example, the length of the tool was used to determine lines in the set of candidates of an suitable length. Also, the tool width was used to determine lines which were the proper distance apart. Also, the slope of the proper lines could be determined since the shaft of the tool would be identified by two substantially parallel lines. Using this domain knowledge in the form of standard IF-ELSE conditions with generic image analysis data, each tool shaft was identified in the image (see FIG. 8).

Tool Location Determination

End points of the identified lines which define the edges of the tools were used for extracting the 2-D coordinates of the tools. Further, using features of the tools, the tool's two-dimensional orientation was determined. By analyzing two corresponding images of the stereoscopic video (taken simultaneously from two different cameras), the three-dimensional location of tool tips and orientation of tools were determined.

Target Representation and Localization Technique Example

This technique uses the concept of "optical flow" to track the apparent motion of objects (in the present case, the surgical tools) in the frames of a video. The optical flow techniques shown in this example, use either the Horn-Schunck method or the Lucas-Kanade method. Other methods are possible and within the scope of this disclosure.

At a high level, the following constraint equation can be used to compute the optical flow between two images:

$$I_x u + I_y v + I_t = 0$$

In this equation, $I_x$, $I_y$, and $I_t$ are the intensity of a pixel at location x, y, t, u is the horizontal optical flow, and v is the vertical optical flow. This equation is under-constrained; however, there are several methods to solve for u and v:

Horn-Schunck Method

By assuming that the optical flow is smooth over the entire image, the Horn-Schunck method computes an estimate of the velocity field that minimizes the global energy functional equation:

$$E = \int\int (I_x u + I_y v + I_t)^2 dx dy +$$
$$\alpha \int\int \left\{ \left(\frac{\partial u}{\partial x}\right)^2 + \left(\frac{\partial u}{\partial y}\right)^2 + \left(\frac{\partial v}{\partial x}\right)^2 + \left(\frac{\partial v}{\partial y}\right)^2 \right\} dx dy$$

The Horn-Schunck method minimizes the previous equation to obtain the velocity field, [u v], for each pixel in the image, which is given by the following equations:

$$u_{x,y}^{k+1} = \bar{u}_{x,y}^k - \frac{I_x[I_x \bar{u}_{x,y}^k + I_y \bar{v}_{x,y}^k + I_t]}{\alpha^2 + I_x^2 + I_y^2}$$

$$v_{x,y}^{k+1} = \bar{v}_{x,y}^k - \frac{I_y[I_x \bar{u}_{x,y}^k + I_y \bar{v}_{x,y}^k + I_t]}{\alpha^2 + I_x^2 + I_y^2}$$

In this equation, $[u_{x,y}^k\ v_{x,y}^k]$ is the velocity estimate for the pixel at (x,y). For k=0, the initial velocity is 0.

A method according to an embodiment of the present invention using Horn-Schunck solves for u and v by computing and using the Sobel convolution kernel and its transposed form for each pixel in the first image. Then, compute between frames 1 and 2 using the kernel. Assume the previous velocity to be 0, and compute the average velocity for each pixel using as a convolution kernel. Finally, iteratively solve for u and v.

Lucas-Kanade Method:

To solve the optical flow constraint equation for u and v, the Lucas-Kanade method divides the original image into smaller sections and assumes a constant velocity in each section. Then, the method performs a weighted least-square fit of the optical flow constraint equation to a constant model in each section by minimizing the following equation:

$$\sum_{x \in \Omega} W^2 [I_x u + I_y v + I_t]^2$$

Here, W is a window function that emphasizes the constraints at the center of each section. The solution to the minimization problem is given by the following equation:

$$\begin{bmatrix} \sum W^2 I_x^2 & \sum W^2 I_x I_y \\ \sum W^2 I_y I_x & \sum W^2 I_y^2 \end{bmatrix} \begin{bmatrix} u \\ v \end{bmatrix} = -\begin{bmatrix} \sum W^2 I_x I_t \\ \sum W^2 I_y I_t \end{bmatrix}$$

The block computes using a difference filter or a derivative of a Gaussian filter (below)

Difference Filter:

Compute and use the kernel and its transposed form. For fixed-point data types, the kernel values are signed, fixed-point values with a word length equal to 16 and fraction length equal to 15.

1. Compute between images 1 and 2 using the kernel.
2. Smooth the gradient components and use a separable and isotropic 5-by-5 element kernel. For fixed-point data types, the kernel values are unsigned, fixed-point values with word length equal to 8 and fraction length equal to 7.
3. Solve the 2-by-2 linear equations for each pixel by:
If $$A = \begin{bmatrix} a & b \\ b & c \end{bmatrix} = \begin{bmatrix} \sum W^2 I_x^2 & \sum W^2 I_x I_y \\ \sum W^2 I_y I_x & \sum W^2 I_y^2 \end{bmatrix},$$

then the eigenvalues of A are $$\lambda_i = \frac{a+c}{2} \pm \frac{\sqrt{4b^2 + (a-c)^2}}{2}; i = 1, 2.$$

In the fixed-point diagrams, $$P = \frac{a+c}{2}, Q = \frac{\sqrt{4b^2 + (a-c)^2}}{2}$$

4. When the eigenvalues are computed, they are compared to a threshold (noise reduction) parameter that is user selectable. Selection is made to eliminate the effect of small movements between frames—the higher the threshold value, the less small movements impact the optical flow calculation. The results fall into one of the following cases:

Case 1: A is nonsingular, so the block solves the system of equations using Cramer's rule.
Case 2: A is singular (noninvertible), so the block normalizes the gradient flow to calculate u and v.
Case 3: The optical flow, u and v, is 0.

Derivative of Gaussian:

Compute and use a Gaussian filter to perform temporal filtering. Specific temporal filter characteristics such as the standard deviation and number of filter coefficients are selected as appropriate.

Compute and use a Gaussian filter and the derivative of a Gaussian filter to smooth the image using spatial filtering. Specific standard deviation and length of the image-smoothing filter are selected as appropriate.

1. Compute between images 1 and 2 using the following steps:

Use the derivative of a Gaussian filter to perform temporal filtering. Specific temporal filter characteristics such as the standard deviation and number of filter coefficients are selected as appropriate.

a. Use a filter to perform spatial filtering on the output of the temporal Filter.

2. Smooth the gradient components and using a gradient smoothing filter. The standard deviation and the number of filter coefficients for the gradient smoothing filter are selected as appropriate.

3. Solve the 2-by-2 linear equations for each pixel using the following method:
If $$A = \begin{bmatrix} a & b \\ b & c \end{bmatrix} = \begin{bmatrix} \sum W^2 I_x^2 & \sum W^2 I_x I_y \\ \sum W^2 I_y I_x & \sum W^2 I_y^2 \end{bmatrix},$$

then the eigenvalues of A are $$\lambda_i = \frac{a+c}{2} \pm \frac{\sqrt{4b^2 + (a-c)^2}}{2}; i = 1, 2$$

4. When the eigenvalues are computed, they are compared to a threshold (noise reduction) parameter that is user selectable. Selection is made to eliminate the effect of small movements between frames—the higher the threshold value, the less small movements impact the optical flow calculation. The results fall into one of the following cases:

Case 1: A is nonsingular, so the block solves the system of equations using Cramer's rule.
Case 2: A is singular (noninvertible), so the block normalizes the gradient flow to calculate u and v.
Case 3: The optical flow, u and v, is 0.

Software Interface

Figure 9A:
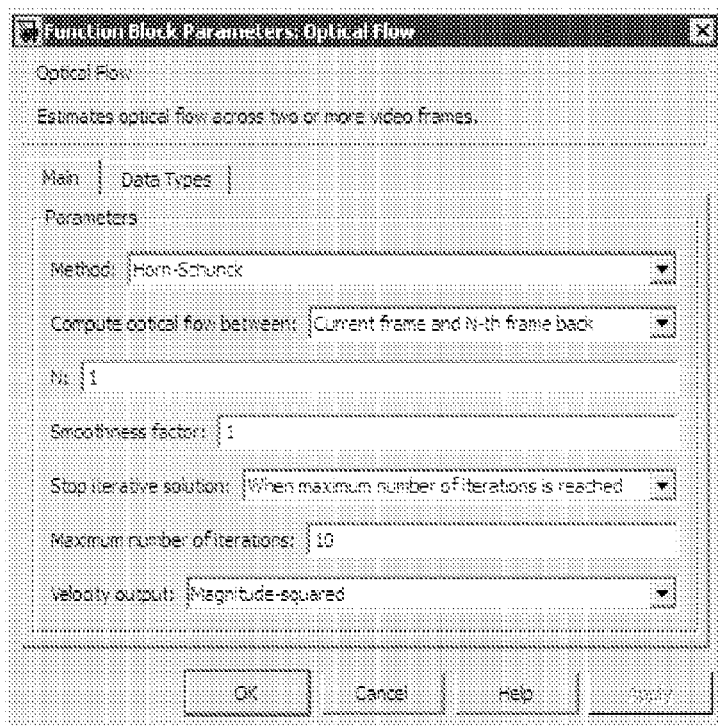
FIG. 9A is a dialog box showing user-selectable parameters for image processing.
Figure 9B:
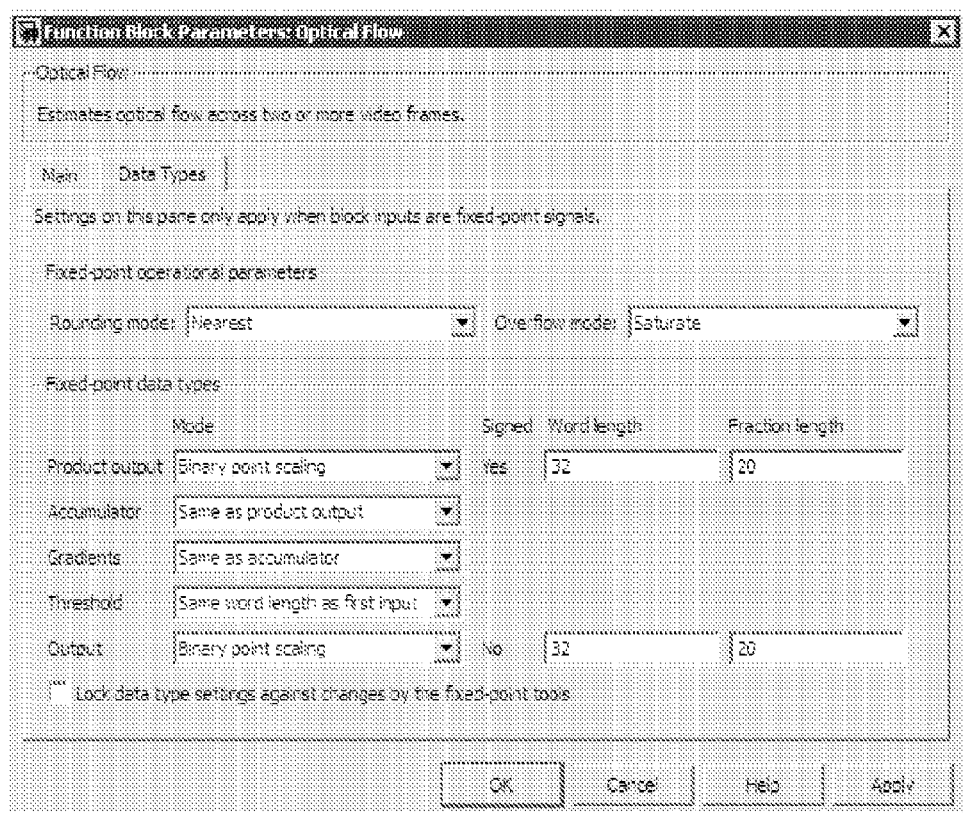
FIG. 9B is another dialog box showing additional user-selectable parameters for image processing.
Figure 10:
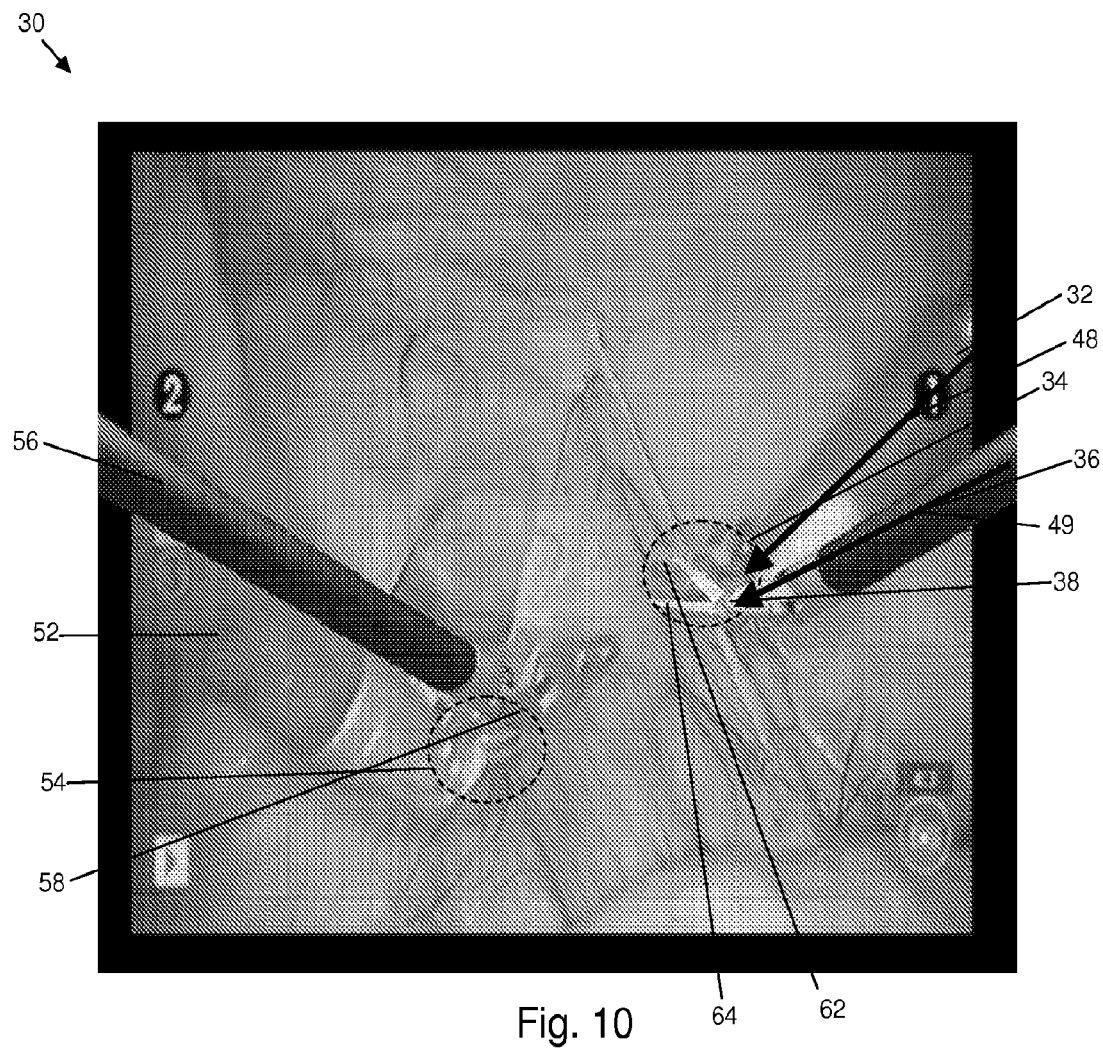
FIG. 10 is an image from a video of an MIS and having virtual tools superimposed for training a trainee.

In a non-limiting example, the aforementioned optical flow techniques were implemented in software. The main pane of the Optical Flow dialog box is shown in FIG. 9A, and the "Data Types" pane is shown in FIG. 9B. The main field parameters are described below.

Method: Select the method the block uses to calculate the optical flow. The choices are "Horn-Schunck" or "Lucas-Kanade."

Compute optical flow between: Select two images to compute the optical flow between two images. Select "Current frame and N-th frame back" to compute the optical flow between two video frames that are N frames apart. This parameter is visible when the Method parameter is set to "Horn-Schunck" or the Method parameter is set to "Lucas-Kanade" and the Temporal gradient filter to "Difference filter [−1 1]."

N: Enter a scalar value that represents the number of frames between the reference frame and the current frame. This parameter becomes available when the Compute optical flow between parameter is set to a selection requiring a value for N.

Smoothness factor: If the relative motion between the two images or video frames is large, enter a large positive scalar value. If the relative motion is small, enter a small positive scalar value. This parameter becomes available when the Method parameter is set to "Horn-Schunck."

Stop iterative solution: Use this parameter to control when the block's iterative solution process stops. If the iteration should stop when the velocity difference is below a certain threshold value, select "when velocity difference falls below threshold." If the iteration should stop after a certain number of iterations, choose "when maximum number of iterations is reached." There is also an option for "whichever comes first." This parameter becomes available when the Method parameter is set to Horn-Schunck.

Maximum number of iterations: Enter a scalar value that represents the maximum number of iterations the block should perform. This parameter is only visible if "when maximum number of iterations is reached" or "whichever comes first" is selected for the Step iterative solution parameter. This parameter becomes available when the Method parameter is set to "Horn-Schunck."

Velocity difference threshold: Enter a scalar threshold value. This parameter is only visible if, for the Stop iterative solution parameter, "When velocity difference falls below threshold" or "Whichever comes first" is selected. This parameter becomes available when the Method parameter is set to "Horn-Schunck."

Velocity output: If "Magnitude-squared" is selected, the block outputs the optical flow matrix where each element is of the Magnitude-squared form. If "Horizontal and vertical components in complex form" is selected, the block outputs the optical flow matrix where each element is of the horizontal and vertical form.

Temporal gradient filter: Specify whether the block solves for u and v using a "difference filter" or a "derivative of a Gaussian filter." This parameter becomes available when the Method parameter is set to "Lucas-Kanade."

Number of frames to buffer for temporal smoothing: Use this parameter to specify the temporal filter characteristics such as the standard deviation and number of filter coefficients. This parameter becomes available when the temporal gradient filter parameter is set to "Derivative of Gaussian."

Standard deviation for image smoothing filter: Specify the standard deviation for the image-smoothing filter. This parameter becomes available when the temporal gradient filter parameter is set to "Derivative of Gaussian."

Standard deviation for gradient smoothing filter: Specify the standard deviation for the gradient smoothing filter. This parameter becomes available when the temporal gradient filter parameter is set to "Derivative of Gaussian."

Discard normal flow estimates when constraint equation is ill conditioned: Select this check box if the block should set the motion vector to zero when the optical flow constraint equation is ill conditioned. This parameter becomes available when the temporal gradient filter parameter is set to "Derivative of Gaussian."

Output image corresponding to motion vectors (accounts for block delay): Select this check box if the block should output the image that corresponds to the motion vector being output by the block. This parameter becomes available when the temporal gradient filter parameter is set to "Derivative of Gaussian."

Threshold for noise reduction: Enter a scalar value that determines the motion threshold between each image or video frame. The higher the number, the less small movements impact the optical flow calculation. This parameter becomes available when the Method parameter is set to "Lucas-Kanade."

The parameters on the Data Types dialog box become visible only when the "Lucas-Kanade" method is selected.

Rounding mode: Select the rounding mode for fixed-point operations.

Overflow mode: Select the overflow mode for fixed-point operations.

Product output: Use this parameter to specify how to designate the product output word and fraction lengths.

When "Binary point scaling" is selected, the word length and the fraction length of the product output in bits may be entered. When "Slope and bias scaling" is selected, the word length in bits and the slope of the product output may be entered. The bias of all signals in the Video and Image Processing Blockset blocks is 0.

Accumulator: Use this parameter to specify how to designate this accumulator word and fraction lengths.

When "same as product output" is selected, these characteristics match those of the product output. When "Binary point scaling" is selected, the word length and the fraction length of the accumulator in bits may be entered. When "Slope and bias scaling" is selected, the word length in bits and the slope of the accumulator may be entered. The bias of all signals in the Video and Image Processing Block setblocks is 0.

Gradients: Choose how to specify the word length and fraction length of the gradients data type. When "same as accumulator" is selected, these characteristics match those of the accumulator. When "same as product output" is selected, these characteristics match those of the product output. When "Binary point scaling" is selected, the word length and the fraction length of the quotient, in bits, may be entered. When "Slope and bias scaling" is selected, the word length in bits and the slope of the quotient may be entered. The bias of all signals in the Video and Image Processing Blockset blocks is 0.

Threshold: Choose how to specify the word length and fraction length of the threshold data type: When "same word length as first input" is selected, the threshold word length matches that of the first input. When "Specify word length" is selected, enter the word length of the threshold data type. When "Binary point scaling" is selected, the word length and the fraction length of the threshold, in bits, may be entered. When "Slope and bias scaling" is selected, the word length in bits and the slope of the threshold may be entered. The bias of all signals in the Video and Image Processing Block set blocks is 0.

Combinations of Techniques

The above example techniques, and others, can be combined in ways which enhance the accuracy and/or lower the processing requirements of the automated tool tracking methods. For example, the video frames may be pre-processed to remove considerable detail before using optical flow techniques to identify the moving objects.

In an exemplary (non-limiting) embodiment of the present invention, the tool location is determined through a combination of these techniques. The video is received by the processor. The frames of the video are preprocessed by reducing the resolution of the video, removing noise and clutter by application of an appropriate filter, thresholding to further reduce the amount of information in the video, and eroding and dilating the objects in the video in order to further consolidate (i.e., simplify) the objects. Optical flow techniques are used on this pre-processed video to detect the movement (velocity) of the features of the video. The moving features are processed to determine regions of interest (i.e., blobs) and the centroids of the blobs are determined in each frame. This centroid is used as a proxy for the overall tool location. In the case of a stereoscopic video, the centroids from each image of a two-image frame are processed using, for example, a Kalman filter to determine the three-dimensional location of the centroid.

The present invention may be embodied as a system 10 for MIS training using a video of an MIS, the video having a plurality of frames, and a first surgical tool is visible in the video. Reference is made to the example of the RoSS device of FIG. 1 (although the system 10 is not limited to a RoSS). The system 10 comprises a processor 24 having a memory 25. The system 10 further comprises a communication device 31 in communication with the processor 24 and capable of receiving a video such that the video may be processed by the processor 24. The communication device 31 may be, for example, a CD drive, a network interface, a tape drive, or other device capable of communicating the video to the processor 24 and/or memory 25. The system 10 also comprises a first input device 16 in communication with the processor 24.

In the system 10 of such embodiments, the processor 24 is programmed perform any or all of the methods previously described. In a particular embodiment, the processor is programmed to process the video to determine a location of the first surgical tool in each of the frames. In this embodiment, the processor 24 is further programmed to display the video and to determine whether the configuration of the first input device 16 substantially corresponds to the location of the first surgical tool in each frame of the video while the video is displayed.

In an embodiment of the present invention, the processor 24 may be programmed to process the video by obtaining physical characteristic data of the first surgical tool using the communication device. The processor 24 is programmed to process a first frame of the video to detect a plurality of features. The processor 24 is programmed to use the physical characteristic data of the first surgical tool to identify at least one tool feature from among the plurality of features. The processor 24 is programmed to calculate a position of the at least one tool feature as the location of the first surgical tool within the first frame.

A system may comprise a second input device 18. In such embodiments, the processor 24 may be further programmed to determine whether the configuration of the second input device 18 substantially corresponds to the location of the second surgical tool in each frame of the video while the video is displayed.

In another embodiment of a system 10, the processor 24 may be further programmed to retrieve physical characteristic data of the at least one surgical tool. The physical characteristic data may include information about the at least one surgical tool such as, but not limited to, color, length, width, diameter, shape, etc. The physical characteristic data may be in a machine-readable format, such as, for example, a delimited file. The processor 24 may be programmed to process a first frame of the video to detect a plurality of features. The processor 24 may be programmed to identify the at least one surgical tool by using the physical characteristic data.

The processor 24 may be programmed to calculate a position of the at least one tool feature in order to determine the location of the at least one surgical tool within the first frame. The processor 24 may be further programmed to repeat each of these programmatic, frame-specific steps for each frame of the video.

In another embodiment, a system 10 may further comprise a data entry device 33 for entry of physical characteristic data of the at least one surgical tool. The data entry device 33 may be, for example, a keyboard, a mouse, a touch pad, a network communication device, or other device capable of communication the physical characteristic data to the processor 24 and/or memory 25. It is contemplated that the communication device 31 and the data entry device 33 may be the same physical device shared for these two purposes (e.g., a network interface card may be used to receive both a file containing the video and a file containing the physical characteristic data).

The present invention may be embodied as a computer program for performing any of the methods described herein. The computer program may be embodied on a computer readable medium. The computer readable medium may be a computer network or a storage location (e.g., server, NAS, SAN, etc) attached to a computer network.

Although the present invention has been described with respect to one or more particular embodiments, it will be understood that other embodiments of the present invention may be made without departing from the spirit and scope of the present invention. There are numerous embodiments of the invention described herein including examples, all of which are intended to be non-limiting examples (whether explicitly described as non-limiting or not). Hence, the present invention is deemed limited only by the appended claims and the reasonable interpretation thereof.

What is claimed is:

1. A method of minimally-invasive surgery ("MIS") training using a video of an MIS, the video having a plurality of frames, and wherein a first surgical tool is visible in the video, the method comprising the steps of:
    (a) providing a processor, a display in communication with the processor, and a first input device in communication with the processor;
    (b) processing the video using the computer to determine a location of the first surgical tool in each of the frames;
    (c) displaying the video on the display;
    (d) determining whether the configuration of the first input device substantially corresponds to the location of the first surgical tool in each frame of the video while the video is displayed.

2. The method of claim 1, wherein the step of processing the video to determine a location of the first surgical tool in each of the frames, comprises the steps of:
    (a) obtaining physical characteristic data of the first surgical tool;
    (b) processing a first frame of the video to detect a plurality of features;
    (c) identifying at least one tool feature from among the plurality of features using the physical characteristic data of the first surgical tool;
    (d) calculating a position of the at least one tool feature as the location of the first surgical tool within the first frame; and
    (e) repeating each of steps (b)-(d) for each subsequent frame of the video.

3. The method of claim 2, wherein the plurality of features are edges, corners, points, regions of interest, or centroids of regions of interest.

4. The method of claim 1, further comprising the step of pausing the video when the configurations of the first input device does not substantially correspond to the location of the first surgical tool.

5. The method of claim 2, wherein the step of processing the first frame of the video further comprises the step of applying one or more image processing filters.

6. The method of claim 5, wherein the one or more image processing filters are selected from the group consisting of blurring filters, Gaussian filters, and median filters.

7. The method of claim 2, wherein the step of processing the first frame of the video further comprises the step of thresholding the image to provide a binary image.

8. The method of claim 2, wherein the step of processing the first frame of the video further comprises using a morphological function to reduce the number of noise pixels.

9. The method of claim 8, wherein the morphological function is an erosion function.

10. The method of claim 8, wherein the morphological function is a dilation function.

11. The method of claim 2, wherein the step of processing the first frame of the video further comprises applying an edge detection function to the first frame of the video and wherein the plurality of features are edges.

12. The method of claim 11, wherein the edge detection function is a Canny function.

13. The method of claim 11, wherein the step of using the physical characteristic data of the at least one surgical tool to identify tool features further comprises the steps of:
    (a) using a Hough transform to determine a set of tool edge candidates; and
    (b) using the physical characteristic data to identify the tool edges from the set of tool edge candidates.

14. The method of claim 1, wherein each frame of the video comprises at least two images each showing a different point of view such that the location of the surgical tool may be determined along a third dimension.

15. The method of claim 1, further comprising the step of writing the location of the at least one surgical tool in each frame of the video to a memory device.

16. The method of claim 1, further comprising the steps of:
    (a) determining the location of a point on the at least one surgical tool in the first frame; and
    (b) recording the location of the point to a memory device; and
    (c) repeating steps (a)-(b) for each frame of the video.

17. The method of claim 15, wherein the point is the most distal point on an edge of the at least one surgical tool.

18. The method of claim 1, wherein the step of processing the video to determine a location of the first surgical tool in each of the frames, comprises the step of processing at least two frames of the video to detect at least one object which changes location from a first frame of the at least two frames to a second frame of the at least two frames.

19. The method of claim 18, wherein the step of processing at least two frames of the video to detect at least one object which changes location, comprises the steps of:
    (a) calculating a velocity field of a plurality of sections of the at least two frames of the video;
    (b) using a pre-determined threshold parameter to identify and combine sections of the at least two frames having similar, non-zero velocity fields into at least one region of interest; and
    (c) determining a centroid of the at least one region of interest as the location of the at least one object.

20. The method of claim 19, wherein the centroid is determined in each frame of the video.

21. The method of claim 18, wherein the plurality of sections is comprised of each pixel of the at least two frames.

22. A system for minimally-invasive surgery ("MIS") training using a video of an MIS, the video having a plurality of frames, and wherein a first surgical tool is visible in the video, the system comprising:
    (a) a processor having a memory;
    (b) a communication device in communication with the processor and capable of receiving a video such that the video may be processed by the processor;
    (c) a first input device in communication with the processor; and
    (d) wherein the processor is programmed to:
        (1) process the video to determine a location of the first surgical tool in each of the frames;
        (2) display the video on the display;
        (3) determine whether the configuration of the first input device substantially corresponds to the location of the first surgical tool in each frame of the video while the video is displayed.

23. The system of claim 22, wherein the processor being programmed to process the video comprises:
    (a) obtaining physical characteristic data of the first surgical tool using the communication device;
    (b) processing a first frame of the video to detect a plurality of features;
    (c) using the physical characteristic data of the first surgical tool to identify at least one tool feature from among the plurality of features;
    (d) calculating a position of the at least one tool feature as the location of the first surgical tool within the first frame; and
    (e) repeating each of steps (b)-(d) for each subsequent frame of the video.

24. A non-transitory computer-readable medium having stored thereon a computer program for instructing a computer to perform the method of claim 1.

* * * * *

UNITED STATES PATENT AND TRADEMARK OFFICE
CERTIFICATE OF CORRECTION

PATENT NO.        : 9,601,025 B2
APPLICATION NO.   : 13/806889
DATED             : March 21, 2017
INVENTOR(S)       : Kesavadas et al.

Page 1 of 1

It is certified that error appears in the above-identified patent and that said Letters Patent is hereby corrected as shown below:

In the Claims

Column 16, Line 43, in Claim 3, "comers" should read:
--corners--; and

Column 17, Line 26, in Claim 17, "claim 15" should read:
--claim 16--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*